United States Patent [19]

Chambers

[11] Patent Number: 5,086,391
[45] Date of Patent: Feb. 4, 1992

[54] REMOTE CONTROLLER FOR ACTIVATING SPEECH MESSAGES AND FOR CONTACTING EMERGENCY SERVICES

[76] Inventor: Bryan R. Chambers, 18197 Useppa Rd., Ft. Myers, Fla. 33912

[21] Appl. No.: 617,942

[22] Filed: Nov. 28, 1990

Related U.S. Application Data

[63] Continuation of Ser. No. 315,111, Feb. 24, 1989, abandoned, which is a continuation-in-part of Ser. No. 106,873, Oct. 13, 1987, abandoned.

[51] Int. Cl.⁵ .................. G08B 21/00; G10L 5/02
[52] U.S. Cl. .................. 364/413.02; 340/539; 340/573; 340/298; 381/51
[58] Field of Search ........... 340/502, 504, 313, 531, 340/539, 298, 573; 364/413.02; 381/51

[56] References Cited

U.S. PATENT DOCUMENTS

| | | | |
|---|---|---|---|
| 3,634,885 | 1/1972 | Barkley | 340/573 |
| 4,215,240 | 7/1980 | Ostrowski | 381/51 |
| 4,560,978 | 12/1985 | Lemelson | 381/51 X |
| 4,563,758 | 1/1986 | Paternostro | 381/51 X |
| 4,589,132 | 5/1986 | Botbol et al. | 381/51 |
| 4,616,214 | 10/1986 | Naito | 340/504 X |
| 4,674,454 | 6/1987 | Phairr | 123/179 B |
| 4,810,216 | 3/1989 | Kawamura | 440/2 |
| 4,828,501 | 5/1989 | Ingenito et al. | 434/265 |
| 4,829,285 | 5/1989 | Brand et al. | 340/539 X |
| 4,833,477 | 5/1989 | Tendler | 342/389 |

OTHER PUBLICATIONS

"The Incredible HUC (aural callouts of customized normal and emergency checklists)", *Business & Commercial Aviation*, vol. 59, Sep. 1986, 168 (2).

*Primary Examiner*—Clark A. Jablon
*Attorney, Agent, or Firm*—Richard C. Litman

[57] ABSTRACT

A medical alert system for domestic use wherein the system is comprised of two major components, a device worn about the neck and a home computer. The device worn about the neck and the home computer reciprocally communicate with one another to provide the wearer of the device, as well as an attendant to the wearer of the device, both instructions for care and a method to call for emergency help. The home computer contains an audio synthesizer and a voice amplification device to communicate verbally to the individual. The device may be used to summons an ambulance from a remote location if a the injured person is unable to reach a telephone. The device may also be actuated by an attitude wherein an emergency call can be made should the individual fall during a heart attack or a seizure.

8 Claims, 3 Drawing Sheets

REMOTE CONTROLLER FOR ACTIVATING SPEECH MESSAGES AND FOR CONTACTING EMERGENCY SERVICES

This is a continuation of co-pending application Ser. No. 07/315,111 filed on Feb. 24, 1989 abandoned, which is a continuation-in-part of the application filed on 10/13/87, Ser. No. 07/106,873 abandoned.

BACKGROUND OF THE INVENTION

1. Field of the Invention

The present invention relates to devices that can be used in the home to provide medical assistance to an injured individual. More specifically, this invention relates to those devices which are microcomputer based and include a microtransmitter to ultimately contact the emergency 911 number. The present invention also relates to those types of devices that can be used to instruct attendant individuals as to the appropriate care to be given to an injured person.

2. Description of the Prior Art

There have been a number of domestic use medical alert systems patented and produced. However, they address the needs of the consumer only partially. The present invention is an improvement over these devices, and it provides a multitude of functions to aid the consumer in his medical needs.

The most basic type of device for medical alert is described in U.S. Pat. No. 3,248,723 issued to K. H. Miethe on Apr. 28, 1966, Miethe discloses an automatically actuated audible alarm. However, the alarm can be heard only by those persons in the immediate vicinity of the injured individual.

A device for the treatment of an individual is described in a rudimentary way in U.S. Pat. No. 3,634,885 issued to J. H. Barkley on Jan. 11, 1972. This particular invention involves the use of a tape recorder and an attitude activated switch. The switch turns a tape recorder on when the individual falls to the ground. The tape recorder provides information for the treatment of the individual based upon his particular medical problem or medical history. As with the previously described invention, the tape recording can only be heard by someone who happens to be near the injured individual. Thus, its scope is limited.

The present invention provides these features in an improved fashion. It adds to these features, and provides a multitude of conveniences to both the owner of the system as well as a person who is attending the owner of the system.

SUMMARY OF THE INVENTION

Therefore, it is an object of the present invention to provide a device that can be carried or worn about the neck that can provide a multitude of functions to aid the injured individual as well as assist an attendant to that individual.

It is another object of the present invention to provide such a device that can be fully sealed so that the individual carrying or wearing the device does not need to be concerned with the internal electronics becoming wet or damaged during the course of a normal day. The best way to accomplish this would be to encapsulate the attached keyboard in an elastomeric material thereby sealing the entire device.

It is still another object of the present invention to provide a home computer that contains a library of information regarding the appropriate care of an injured individual given certain conditions such as burning, bleeding, heart attacks, and poisoning.

It is another object of the present invention to provide a microtransmitter and microreceiver within the device that can reciprocally communicate with the home computer which has a complementary transmitter and receiver.

It is yet another object of the present invention to provide a voice synthesizer to the home computer such that the library information concerning the care of individuals may be audibly broadcast to an attendant individual.

It is still another object of the present invention to provide a telecommunications link to a telephone line so that, when instructed, the home computer can contact the emergency 911 number and relay vital information to the response center. Specifically, the information relayed would include the name and address of the individual. This feature is designed to expedite the dispatch of an ambulance to aid a person who is not able to contact an emergency service.

It is an additional object of the present invention to provide a pictorial keypad on the device worn about the neck which functions to provide the wearer or the attendant selection of the appropriate library information stored in the home computer, and includes the emergency call activator to start the sequence of events to contact 911.

It is yet another object of the present invention to provide a means to relay medical information to a hospital or rescue center to aid in the appropriate diagnosis and treatment of the injured individual.

It is another object of the present invention to provide an attitude activated switch for the device worn about the neck such that if the person should have a seizure or heart attack and become unconscious, the device will automatically summon help.

It is yet another object of the present invention to be able to provide emergency help to more than one individual by use of the same home computer. This would be particularly important to those families that have more than one person with failing health. The system could also be used to provide medical protection for all of the members of a family. Should any of them be injured while home alone, he would have rapid access to emergency help.

It is another object of the present invention to provide medical help to an infant, especially should there develop a problem with the child during the night when the parents are asleep. Should the infant become ill or fall prey to some misfortune, the system could be programmed to alert both the parents and an emergency medical organization.

With these and other objects in view which will more readily appear as the nature of the invention is better understood, the invention resides in the novel combination and arrangement of parts hereinafter more fully described and illustrated, with reference being made to the accompanying drawings.

BRIEF DESCRIPTION OF THE DRAWINGS

Similar reference characters designate corresponding parts throughout the various figures of the drawings.

DESCRIPTION OF THE PREFERRED EMBODIMENT

Figure 1:
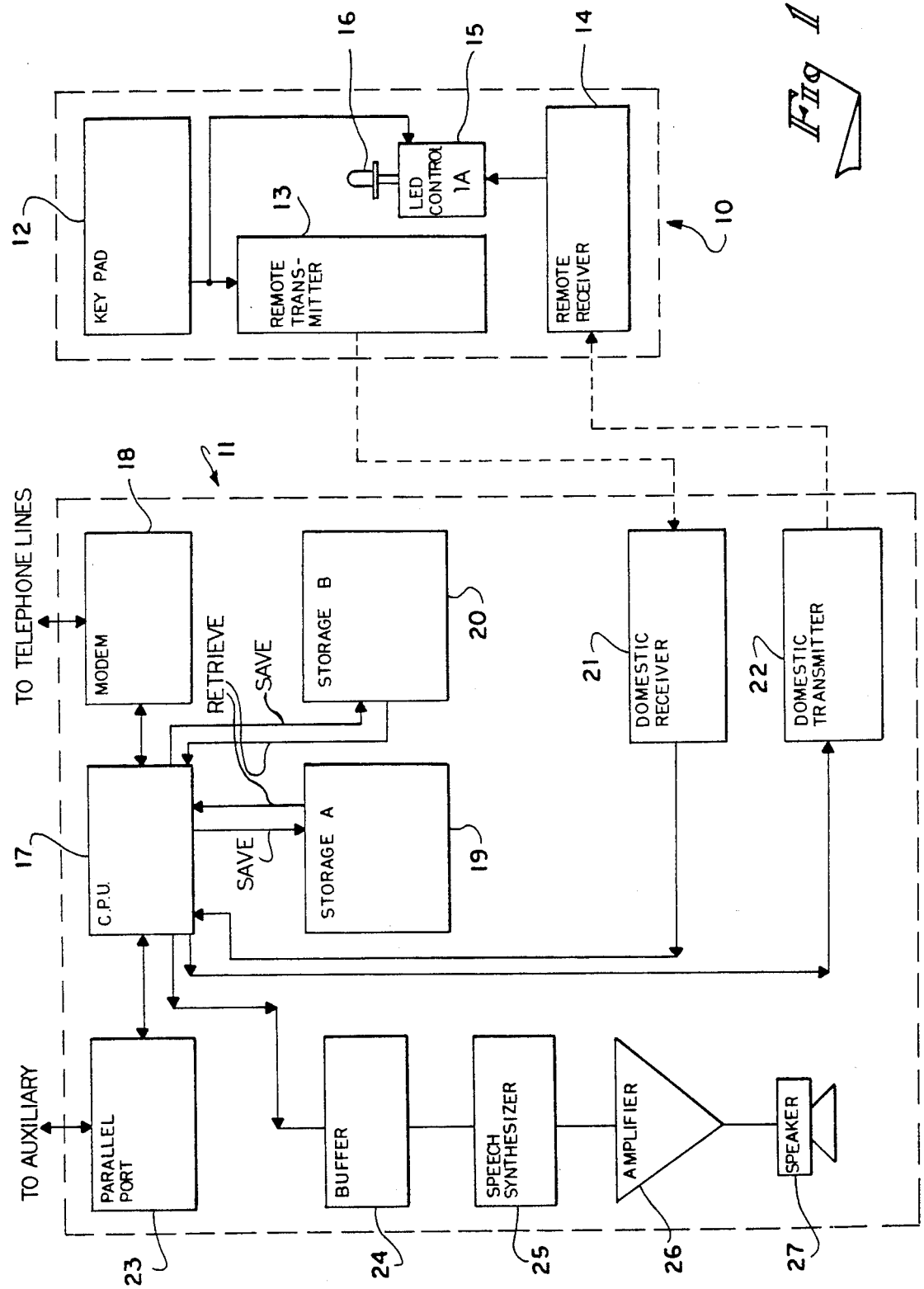
FIG. 1 is a schematic diagram of the components of the medical alert system.
Figure 2:
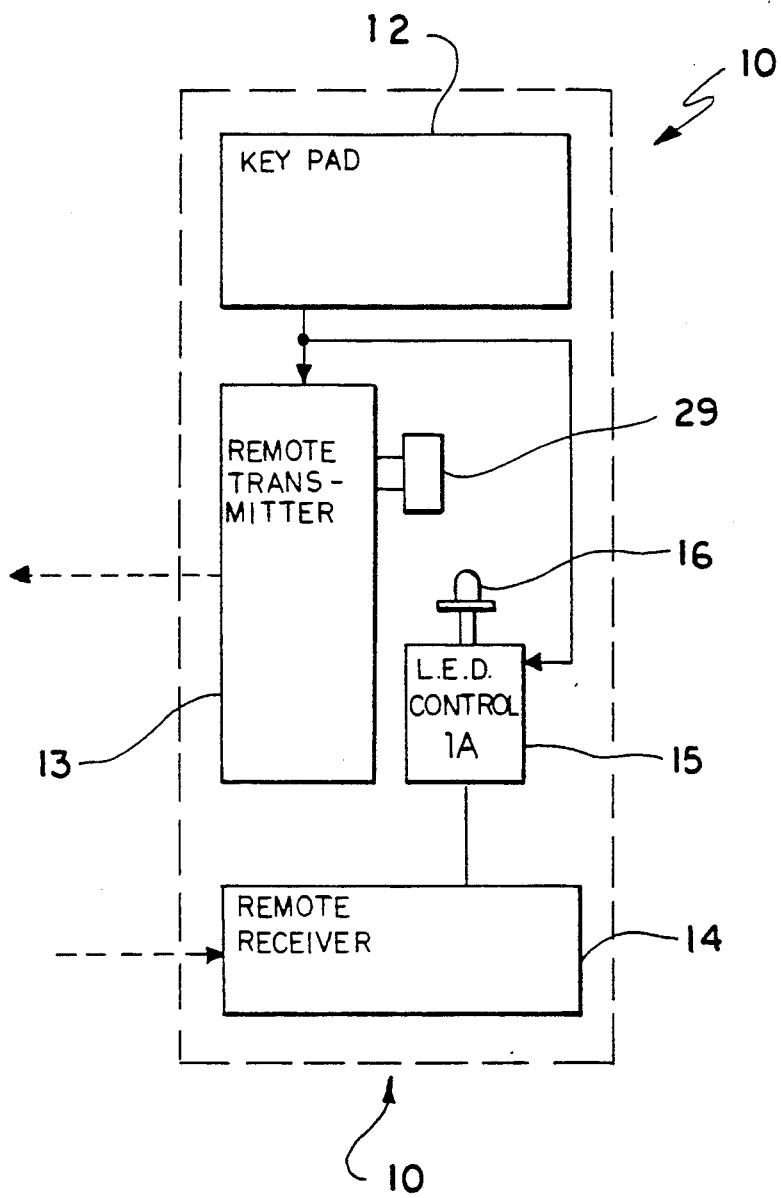
FIG. 2 is a schematic diagram of an alternate embodiment of the remote key pad. The feature of importance is the attitude actuated switch.

The schematic of the present invention is presented in FIG. 1. In order to fully describe the present invention, the description will be divided into two separate parts. Part I is a description of the connection of the various components that compose the present invention. Part II describes the components as they operate in coordination with one another.

PART I

The Apparatus

The home computer is designated by 11 in FIG. 1. The home computer 11 is comprised of a central processing unit (C.P.U.) 17 connected to a variety of other components. The C.P.U. 17 is the main active memory within which all processing and program manipulation occurs.

The C.P.U. 17 is reciprocally connected to a modem 18 such that it can connect with a peripheral computer at a remote location. The modem 18 is connected to existing telephone lines for reciprocal communication. The C.P.U. is also connected to at least one parallel port 23. This parallel port 23 can be used to connect the home computer 11 to an auxiliary device such as another computer or a printer or the like.

The C.P.U. 17 is the active RAM memory in which all programs are run. As a result, the C.P.U. 17 is connected to permanent memory storage devices, storage A 19 and storage B 20. Of course, the computer 11 may contain any number of storage devices that may be required. The storage devices such as storage A 19 and storage B 20 may take the form of hard disk drives, floppy drives, compact disk drives, or whatever storage means may be the mainstay of the current technology.

The storage devices, 19 and 20, reciprocally communicate with the C.P.U. 17. This allows the C.P.U. 17 to retrieve files from the storage devices, 19 and 20, as well as save material therein.

The C.P.U. 17 is also connected to a buffer memory 24. The buffer 24 holds the electronic signals from the C.P.U. 17 before processing by the speech synthesizer 25 to which the buffer 24 is connected. The speech synthesizer 25 interprets the electronic signals stored in the buffer 24 and translates them to audio voice signals that can be interpreted by the human ear. The voice signals from the speech synthesizer 25 are then sent to the amplifier 26 to which the speech synthesizer 25 is connected. The amplifier 26 is connected to a speaker 27 that can broadcast the voice messages.

The C.P.U. is additionally connected to both a computer receiver 21 and a computer transmitter 22. The computer receiver 21 receives signals from the remote 10 and sends them to the C.P.U. 17 for analysis. A return signal is sent by C.P.U. 17 to the computer transmitter 22 which passes the signal back to the remote 10.

Figure 3:
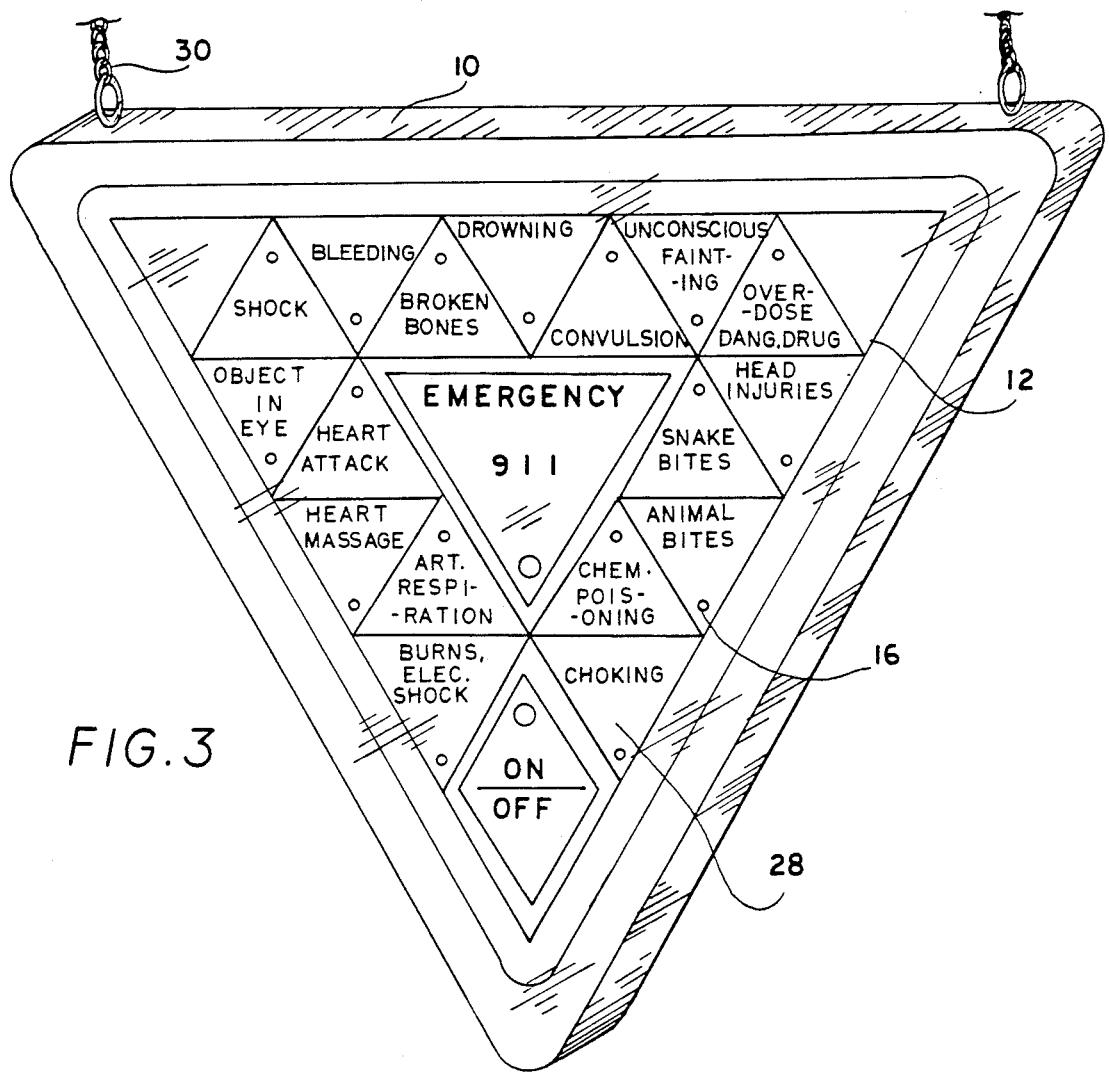
FIG. 3 is a pictorial perspective of the remote device that can be worn about the neck. This is solely an envisioned construction of the device and is not to be construed as a design limitation upon the present invention.

The remote 10 is comprised of relatively few components, yet it is the major component of the interactive system herein described. The remote 10 has a key pad 12 that contains buttons 28 pertinent to its operation as shown in FIG. 3. The key pad 12 is connected both to the remote microtransmitter 13 and the L.E.D. (Light Emitting Diode) controller 15. When a button 28 is depressed, a signal is sent to both the remote microtransmitter 13 and the L.E.D. controller 15. The L.E.D. controller is connected to the many L.E.D.s 16 that are contained on the face of the remote 10, also shown in FIG. 3. Also connected to the L.E.D. controller 15 is the remote microreceiver 14. The remote microreceiver 14 receives signals from the computer transmitter 22 and supplies a signal to the L.E.D. controller 15.

PART II

Operation

The operation of the present invention is fairly simple. In order to best describe the function, the sequence of events that would transpire upon activation of the system will be described.

When one presses a button 28 on the key pad 12 of the remote 10, a signal is sent to the remote microtransmitter 13. The signal corresponds to the button 28 pushed, and each button 28 will have a unique and distinguishing signal characteristic. At the same time, a signal is sent to the L.E.D. controller 15. The signal sent to the L.E.D. controller 15 causes the L.E.D. to flash intermittently. This flashing tells the user that the signal is being processed through the computer 11.

The remote microtransmitter 13 receives the signal from the key pad 12 and sends the signal to the computer 11 via the computer receiver 21. The computer receiver 21, in turn, sends the signal to the C.P.U. 17 for analysis and processing.

At this point, the C.P.U. 17 calculates an appropriate action from its programming what recourse to take. On the key pad 12 there are a number of possible selections. These selections can be broken down into three separate categories: 1) an emergency call, 2) a request for audio assistance, and 3) an on/off signal. Based upon the type of signal the computer receives, it will select the appropriate action. The selection is made through a simple program wherein each signal is coupled with an appropriate response. When the C.P.U. 17 receives a signal it is coupled with its corresponding response and processed accordingly.

If the user has pressed the on/off button, the computer C.P.U. 17 will acknowledge that the remote 10 has been activated by sending a signal back to the remote 10 via the remote microreceiver 14. Thereupon, the remote microreceiver 14 sends a signal to the L.E.D. controller 15 to cause the appropriate L.E.D. 16 to remain lit continuously. The C.P.U. 17 will remain ready and alert to receive any incoming signals from that point. Should the C.P.U. 17 not return a signal for whatever reason, the user will see that the L.E.D. 16 is continuously flashing. At this point, he will know that there is a problem with the computer 11 and effect repairs.

If the C.P.U. 17 receives an "Emergency 911" signal from the remote 10 the action process is different. The C.P.U. 17 interprets this signal, and sends a message to the modem 18 with the appropriate information to dial the emergency 911 number. Once contacted, the C.P.U. 17 will transmit pertinent information relating to the name, address and age of the person injured. As a result, the 911 rescue team can be quickly and effectively dispatched.

As in the previous example, the C.P.U. 17 will send a signal to the computer transmitter 22 that will be passed to the remote microreceiver 14. The remote microreceiver 14 communicates with the L.E.D. controller 15 to cause the appropriate L.E.D. 16 to remain constantly lit. This informs the user the call has been made and that help is on the way.

In addition to sending a signal to the L.E.D. controller 15, the C.P.U. 17 also sends a different signal through the remainder of its circuitry. The C.P.U. 17 will retrieve a message from either storage A 19 or storage B 20. Thereupon it sends the retrieved message to the buffer 24. The buffer 24 holds the message for interpretation by the speech synthesizer 25. The speech synthesizer 25 transforms the electronic signal from the buffer 24 into an audio message. The speech synthesizer 25 sends this message through the amplifier 26 to the speaker 27. The message may contain the following words, "An emergency call has been processed. Help is on the way." This message will further confirm the user's request for assistance.

If the user should press one of the remaining buttons 28 on the key pad 12, the C.P.U. 17 will react accordingly. When the signal is received from the remote 10 via the computer receiver 21, the C.P.U. 17 will retrieve the appropriate message from its storage memory, either 19 or 20. It will then send a signal to the remote 10 in the same manner as described above to cause the appropriate L.E.D. 16 to remain continuously lit. The C.P.U. 17 will send an audio message through the path to the speaker 27 where the message can be heard. The message will contain instructions for the user to assist the injured victim.

The messages that can be encoded into the computer 11 storage memory, either 19 or 20, are numerous. An example is provided below:

"For minor burns:
1. Immerse in clean ice water for ten minutes.
2. Apply a clean, no-stick bandage.
3. Take the victim to the doctor, if needed."

"For serious burns:
1. Press 911.
2. Keep patient lying down with legs elevated.
3. If awake, give liquids to drink.
4. Do not apply anything to the burn area.
5. Watch for shock."

A corresponding message could be provided for any number of common injuries. The following list suggests a possible compendium of the injuries for which a message could be provided. However, the list is not intended to be limited thereto.

Injuries:
1. Shock
2. Bleeding
3. Broken bones
4. Drowning
5. Convulsions
6. Fainting or Unconsciousness
7. Dangerous drugs/Overdoses
8. Head injuries
9. Poisonous snake bites
10. Animal bites
11. Foreign objects in eye
12. Heart attack
13. Chemical poisoning
14. Burns and electrical shocks
15. Choking Additional messages could be included to assist in the application of first aid techniques such as artificial respiration and CPR (CardioPulmonary Resuscitation).

It is possible through the embodiment or the present invention to connect the computer 11 with other computers through the modem 18. In this manner, it might be possible to request information from a library of information at a remote location. For example, a hospital might keep a library of all types of first aid and medical aid on record. A person could access this information through the computer 11. This would be especially important for those non-emergency situations such as a fever where aid is needed but is not needed immediately. An individual could access this information through his home medical system.

In an alternate embodiment of the remote 10, there could be included a attitude actuated switch 29. This switch 29 would cause the activation of the emergency call should the remote key pad 10 be turned on its side. This would be useful for patients that are susceptible to heart attacks. Should the person be alone and suffer a coronary collapse, the remote 10 will automatically notify the appropriate authorities of the trouble. A remote 10 with the attitude switch 29 should be worn about the neck on a chain 30 so that the remote key pad 10 remains vertically aligned at all times. Should the person bend over, the remote 10 will swing forward on the chain 30 and remain vertical, thus preventing any inadvertent summoning of emergency help.

It is to be understood that the present invention is not limited to the sole embodiment described above, but encompasses any and all embodiments within the scope of the following claims.

I claim:

1. An emergency aid device for giving messages concerning medical emergencies comprising:

a computer, said computer including a central processing unit wherein a program is executed, memory means connected to said central processing unit for storing and retrieving data, at least one parallel port connected to and reciprocally communicating with said central processing unit, buffer means connected to said central processing unit for temporarily storing signals from said central processing unit, speech synthesizing means connected to said buffer means for translating said signals received from said buffer means into human speech patterns, receiver means connected to said central processing unit for receiving communication signals and transferring said signals to said central processing unit, and transmitter means connected to said central processing unit for transmitting communication signals from said central processing unit;

modem means connected to said central processing unit for reciprocal interaction between said central processing unit and central processing units remote from said central processing unit through telephone transmission lines;

amplifier means connected to said synthesizing means to amplify said human speech patterns;

speaker means electrically connected to said amplifier means for making said human speech patterns audible to the human ear;

remote control means, for remotely directing the actions of the computer, said remote control means including remote transmitter means for providing communication signals to said receiver means connected to said central processing unit, remote receiver means for receiving communication signals from said transmitter means connected to said central processing unit, a plurality of individually actuatable selection means for selecting specific communication signals to be transmitted through said remote transmitter means to said receiver means connected to said central processing unit, illumination means connected to each said selection means, and illumination control means connected to said illumination means and to said remote receiver means, said illumination control means controls said illumination means according to actuation of each of said selection means and to signals received through said remote receiver means from said transmitter means connected to said central processing unit; and said remote control means carried upon the body of a user for ready access; whereby upon actuation of one of said selection means, said actuated one of said selection means transmits a respective signal through said remote transmitter means to said receiver means connected to said central processing unit, said central processing unit retrieves data from said memory means corresponding to said respective signal and said data is audibly transmitted through said speaker means, and upon actuation of a second selection means, prestored data comprising personal data pertaining to said user is transmitted through said telephone transmission lines to said remote central processing units.

2. A device as set forth in claim 1 wherein each of said selection means of said remote control means includes a front surface face, and wherein each of said illumination means respective to each said selection means is embedded in said respective selection means face for signaling to the user that said central processing unit has been activated and is executing said control program.

3. A device as set forth in claim 2 wherein each of said selection means contains on each said face indicia indicating its function.

4. A device as set forth in claim 3 wherein said remote control means includes an attitude actuated switch for sensing the attitude of the user, said switch connected to said remote transmitter means for transmitting a specific signal to said receiver connected to said central processing unit, said central processing unit retrieving respective said prestored data from said memory means and then transmitting said prestored data through said telephone transmission lines to said remote central processing units.

5. In a device as set forth in claim 4 wherein said remote control means includes attachment means for attaching said remote control means to the neck of said user in a freely suspending manner; said remote control means and said attachment means configured to preclude unintentional actuation of said attitude actuated switch means.

6. In a device as set forth in claim 5, wherein one of said selection means transmits on and off signals to said central processing unit, one of said selection means is an activation means for transmission of said prestored data through said telephone transmission lines, and the remainder of said selection means are activation means for audible broadcast of said respective data through said speaker means.

7. In a device as set forth in claim 3, wherein one of said selection means transmits on and off signals to said central processing unit, one of said selection means is an activation means for transmission of said prestored data through said telephone transmission lines, and the remainder of said selection means are activation means for audible broadcast of said respective data through said speaker means.

8. A method for providing medical emergency assistance comprising the steps of:

providing a computer having a central processing unit wherein a program is executed, said central processing unit including memory means for storing and retrieving data and a control program to be executed;

connecting at least one parallel port means to said central processing unit for reciprocal connection of peripherals to said port means;

connecting modem means to said central processing unit to allow reciprocal interaction between said central processing unit and central processing units remote from said computer through telephone transmission lines;

connecting receiver means and transmitter means to said central processing unit for receiving and transmitting communication signals;

connecting buffer means, synthesizer means, amplifier means and speaker means to said central processing unit to receive, synthesize, amplify and broadcast data received from said central processing unit in recognizable human speech patterns audible to the human ear;

providing remote control means including remote transmitter means and remote receiver means for reciprocal communication with said receiver means and transmitter means connected to said central processing unit;

providing said remote control means with a plurality of individually actuatable selection means to transmit respective signals through said remote transmitter means to said receiver means to said central processing unit to actuate said program;

providing said selection means with indicia to visually indicate to a user the function of each said selection means, one of said indicia being an on/off indication, one of said indicia being an automatic emergency communication indication, and the remainder of said indicia indicating a specific medical condition; and pressing desired ones of said selection means to cause said central processing unit to retrieve said data from said memory means and said computer to audibly broadcast said data or transmit prestored data through said modem means to said remote central processing units; whereby in a situation where a person requires medical attention, medical treatment information is audibly broadcast to person in the vicinity of the person requiring medical attention or medical personnel may be automatically contacted by said computer.

* * * * *